United States Patent
Miyai et al.

(10) Patent No.: US 11,033,225 B2
(45) Date of Patent: Jun. 15, 2021

(54) BRAIN ACTIVITY FEEDBACK SYSTEM

(71) Applicants: Ichiro Miyai, Osaka (JP); Masahito Mihara, Okayama (JP); Shimadzu Corporation, Kyoto (JP)

(72) Inventors: Ichiro Miyai, Hyogo (JP); Masahito Mihara, Osaka (JP); Akihiro Ishikawa, Kyoto (JP); Yoshihiro Inoue, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 620 days.

(21) Appl. No.: 15/576,791

(22) PCT Filed: May 27, 2015

(86) PCT No.: PCT/JP2015/065270
§ 371 (c)(1),
(2) Date: Nov. 24, 2017

(87) PCT Pub. No.: WO2016/189701
PCT Pub. Date: Dec. 1, 2016

(65) Prior Publication Data
US 2018/0303410 A1 Oct. 25, 2018

(51) Int. Cl.
*A61B 5/1455* (2006.01)
*A61B 5/00* (2006.01)
(Continued)

(52) U.S. Cl.
CPC ............ *A61B 5/486* (2013.01); *A61B 5/0042* (2013.01); *A61B 5/0064* (2013.01);
(Continued)

(58) Field of Classification Search
None
See application file for complete search history.

(56) References Cited

U.S. PATENT DOCUMENTS 6,723,047 B1 4/2004 Yamamoto et al.
7,186,217 B2 3/2007 Kawasaki
(Continued)

FOREIGN PATENT DOCUMENTS

JP 3661645 B2 6/2005
JP 3916985 B2 5/2007
(Continued)

OTHER PUBLICATIONS

Extended European Search Report dated Jan. 28, 2019, including the Supplementary European Search Report and the European Search Opinion, in connection with corresponding EP Application No. 15893335.8 (7 pgs.).
(Continued)

*Primary Examiner* — Eric F Winakur
*Assistant Examiner* — Marjan Fardanesh
(74) *Attorney, Agent, or Firm* — Maier & Maier, PLLC (57) ABSTRACT

This brain activity feedback system includes a brain activity measurement device to optically measure brain activity; a data processor to calculate, on the basis of measurement data from the brain activity measurement device, a statistic that indicates the statistical significance of changes in the measurement data; and a display device to display, in real time, a brain activity index corresponding to the statistic. The data processor calculates the statistic for the measurement data from the brain activity measurement device by correcting the scalp blood flow component of the measurement data in real time on the basis of scalp blood flow data.

7 Claims, 4 Drawing Sheets

(51) Int. Cl.
*A61B 10/00* (2006.01)
*A61B 5/026* (2006.01)
*G16H 40/63* (2018.01)
*G16H 50/30* (2018.01)
*G16H 50/20* (2018.01)

(52) U.S. Cl.
CPC .......... *A61B 5/0261* (2013.01); *A61B 5/1455* (2013.01); *A61B 5/14552* (2013.01); *A61B 5/14553* (2013.01); *A61B 5/443* (2013.01); *A61B 5/6814* (2013.01); *A61B 5/7203* (2013.01); *A61B 5/7264* (2013.01); *A61B 5/7275* (2013.01); *A61B 5/742* (2013.01); *A61B 10/00* (2013.01); *A61B 2505/09* (2013.01); *A61B 2562/0233* (2013.01); *G16H 40/63* (2018.01); *G16H 50/20* (2018.01); *G16H 50/30* (2018.01)

(56) References Cited

U.S. PATENT DOCUMENTS

| | | | |
|---|---|---|---|
| 7,231,240 | B2 | 6/2007 | Eda et al. |
| 9,498,158 | B2 * | 11/2016 | Isaacson ............ A61B 5/14553 |
| 2009/0299160 | A1 | 12/2009 | Moridaira et al. |
| 2013/0102907 | A1 | 4/2013 | Funane et al. |

FOREIGN PATENT DOCUMENTS

| | | |
|---|---|---|
| JP | 3928051 B2 | 6/2007 |
| JP | 3952275 B2 | 8/2007 |
| JP | 2008-64675 A | 3/2008 |
| JP | 2009-285008 A | 12/2009 |
| JP | 2010-240298 A | 10/2010 |
| JP | 4561524 B2 | 10/2010 |
| JP | 2011-010714 A | 1/2011 |
| JP | 4722627 B2 | 7/2011 |
| WO | 2012/005303 A1 | 1/2012 |

OTHER PUBLICATIONS

Office Action dated Nov. 28, 2019, in corresponding Chinese Application No. 201580080434.X; 17 pages.
Japanese Office Action dated Nov. 20, 2018, in connection with corresponding JP Application No. 2017-520163 (7 pgs., including machine-generated English translation).
Masahito Mihara et al., "Neurofeedback Using Real-Time Near-Infrared Spectroscopy Enhances Motor Imagery Related Cortical Activation", PLOS ONE, Mar. 2012, p. 1-13, vol. 7, Issue 3, e32234; 13 pgs.
Masahito Mihara et al., "Near-infrared Spectroscopy-mediated Neurofeedback Enhances Efficacy of Motor Imagery-based Training in Poststroke Victims", Stroke, Apr. 2013, p. 1091-1098 with supplemental material; 20 pgs.
International Search Report dated Aug. 11, 2015 of corresponding International application No. PCT/JP2015/065270; 4 pgs.
Written Opinion by the International Search Authority dated Aug. 11, 2015 of corresponding International application No. PCT/JP2015/065270 with the ISR English translation; 6 pgs.

* cited by examiner

EXAMPLE OF DESIGN MATRIX (MATRIX X)

FIG.6

BRAIN ACTIVITY FEEDBACK SYSTEM

TECHNICAL FIELD

The present invention relates to a brain activity feedback system, and in particular, relates to a brain activity feedback system in which a measurement result of brain activity according to a brain activity measurement device is displayed and is fed back to a subject.

BACKGROUND ART

In the related art, a measurement result of brain activity using a brain activity measurement device is displayed and is fed back to a subject (for example, refer to Non-Patent Documents 1 and 2).

In Non-Patent Document 1 of the present inventors, a system is disclosed in which brain activity having motor recollection as a task is measured by using a brain activity measurement device using a near-infrared spectroscopy (NIRS), a statistic determining statistical significance of brain activity measurement data is calculated, and the obtained statistic is displayed on a display unit and is fed back to a subject, in real time.

In addition, in Non-Patent Document 2, it is described that a statistic calculated from a measurement result of brain activity is displayed and fed back, in real time, to a stroke patient having motor paralysis, and thus, brain activity relevant to motor can be enhanced, and the recovery of a motor function can be accelerated. For this reason, a brain activity feedback system is considered to be used in rehabilitation for motor function recovery, or the like.

Non-Patent Document 1: Neurofeedback Using Real-Time Near-Infrared Spectroscopy Enhances Motor Imagery Related Cortical Activation: PloS one [2012], 7(3): e32234

Non-Patent Document 2: Near-infrared Spectroscopy-mediated Neurofeedback Enhances Efficacy of Motor Imagery-based Training in Poststroke Victims: A Pilot Study: Stroke. 2013 April; 44(4): 1091-1098

However, in a case where the brain activity feedback system is used in the rehabilitation for the motor function recovery, there is a case where the measurement result affected by a scalp blood flow according to the condition or the environment of the subject (a patient). That is, in an optical brain activity measurement device, the subject is irradiated with measurement light from the scalp, and a hemoglobin concentration change in the blood in the brain is measured, and thus, a skin blood flow change (the hemoglobin concentration change) when the measurement light passes through the scalp affects the measurement result, and measurement accuracy decreases. For this reason, it is required that the statistic (that is, a brain activity index) can be fed back to the subject (the patient) without decreasing the accuracy even in real time.

SUMMARY

The invention has been made in order to solve the problems described above, and an object of the invention is to provide a brain activity feedback system in which a brain activity index can be fed back to a subject without decreasing accuracy even in real time.

In order to attain the object described above, a brain activity feedback system according to one aspect of the invention, includes: a brain activity measurement device optically measuring brain activity of a subject; a data processing unit calculating a statistic representing statistical significance of a change in measurement data, which is acquired from the brain activity measurement device and reflects the brain activity, on the basis of the measurement data; and a display unit feeding back a brain activity index corresponding to the statistic to the subject by displaying the brain activity index, in real time, in which the data processing unit is configured to correct a scalp blood flow component of the measurement data on the basis of scalp blood flow data, in real time, and calculate the statistic, with respect to the measurement data acquired from the brain activity measurement device. Furthermore, in the invention, the brain activity index is a broad concept including not only the statistic, but also an index, a mark, a graph, and other displays for feedback, reflecting the statistic. In addition, the scalp blood flow data is a broad concept including not only data (an absolute amount) of a scalp blood flow amount, but also data (a relative amount) reflecting a scalp blood flow such as a change amount of the scalp blood flow.

In the brain activity feedback system according to one aspect of the invention, as described above, the data processing unit is configured to correct the scalp blood flow component of the measurement data on the basis of the scalp blood flow data, in real time, and calculate the statistic, with respect to the measurement data acquired from the brain activity measurement device, and thus, even in a case where the brain activity index is fed back (displayed) in real time, according to rehabilitation, it is possible to correct the scalp blood flow component of the measurement data in real time and to calculate the statistic. As a result thereof, the statistic in which the scalp blood flow component is corrected is calculated in real time, and the brain activity index corresponding to the statistic can be displayed, and thus, it is possible to feed back the brain activity index to the subject without decreasing accuracy even in real time.

In the brain activity feedback system according to one aspect of the invention, it is preferable that the brain activity measurement device includes a first measurement channel acquiring the measurement data by a light transmitting probe and a light receiving probe which are arranged in a cephalic portion of the subject with a predetermined first distance, and a second measurement channel acquiring the scalp blood flow data by the light transmitting probe and the light receiving probe which are arranged in the cephalic portion of the subject with a second distance less than the first distance, and the data processing unit is configured to correct the scalp blood flow component in the measurement data of the first measurement channel, on the basis of the scalp blood flow data of the second measurement channel. According to such a configuration, by providing the second measurement channel with the second distance shorter than the first distance for detecting a change in the brain blood flow amount, it is possible to obtain the measurement data (the scalp blood flow data) reflecting the scalp blood flow of measurement light which has passed through the scalp without reaching the brain. Accordingly, it is possible to acquire both of the measurement data of the brain activity and the scalp blood flow data by the common brain activity measurement device without providing a dedicated device for measuring the scalp blood flow data. In addition, it is possible to acquire the scalp blood flow data along with the measurement data of the brain activity, and thus, it is possible to accurately correct the scalp blood flow component even in real time.

In this case, it is preferable that the second distance has a size of less than or equal to ½ of the first distance. According to such a configuration, the measurement light is capable of passing through only an extremely shallow range from the scalp, and thus, it is possible to obtain the scalp blood flow data which more accurately reflects the scalp blood flow. As a result thereof, it is possible to more accurately correct the scalp blood flow component.

In a configuration in which the brain activity measurement device includes the first measurement channel and the second measurement channel, it is preferable that the data processing unit is configured to calculate a correction amount of the scalp blood flow component in which a size is normalized, on the basis of the scalp blood flow data of the second measurement channel in a predetermined time range, and the measurement data of the first measurement channel in the predetermined time range. Here, the measurement data obtained from each of the measurement channels is a relative change amount of a hemoglobin concentration, and thus, there is a case where a signal vibration amplitude or the like is different according to a measurement site. Therefore, by calculating the correction amount of the scalp blood flow component in which the size is normalized, it is possible to suitably correct the scalp blood flow component of the first measurement channel in different measurement sites from the local scalp blood flow data of the second measurement channel.

In a configuration in which the brain activity measurement device includes the first measurement channel and the second measurement channel, it is preferable that the brain activity measurement device includes a plurality of second measurement channels, and the data processing unit is configured to calculate a first main component obtained by performing main component analysis with respect to the scalp blood flow data of the plurality of second measurement channels as a correction amount of the scalp blood flow component. According to such a configuration, for example, by using the first main component extracted from the scalp blood flow data of the plurality of second measurement channels, unlike the case of using local data of one site, it is possible to correct the scalp blood flow component without depending on the local scalp blood flow change. In addition, it is possible to increase a data point used for calculating the correction amount, and thus, it is possible to more accurately correct the scalp blood flow component.

In the brain activity feedback system according to one aspect of the invention, it is preferable that the display unit is configured to change at least one of a shape and a color of a display representing the statistic, and thus, display a change in the statistic as the brain activity index, in real time. According to such a configuration, it is possible to easily visually grasp a temporal change in the brain activity, and thus, it can be expected to improve the motivation of the rehabilitation with respect to the subject (the patient).

In the brain activity feedback system according to one aspect of the invention, it is preferable that the data processing unit is configured to acquire the measurement data in a plurality of sites in a predetermined area of concern, and display the brain activity index corresponding to the maximum statistic on the display unit, from the statistic of the measurement data of the plurality of sites. According to such a configuration, it is possible to feed back the brain activity index in a simple and easy-to-grasp manner, to the subject (the patient), even in the case of calculating the statistic for each of a plurality of measurement channels. As a result thereof, it is possible to easily immediately grasp the brain activity, and thus, it can be expected to improve the motivation of the rehabilitation with respect to the subject (the patient).

According to the invention, as described above, it is possible to feed back a brain activity index to a subject without decreasing accuracy even in real time.

DETAILED DESCRIPTION

Hereinafter, an embodiment in which the invention is embodied will be described on the basis of the drawings.

First, the entire configuration of a brain activity feedback system 100 according to one embodiment of the invention will be described with reference to FIG. 1 to FIG. 6.

[Configuration of Brain Activity Feedback System]

Figure 1:
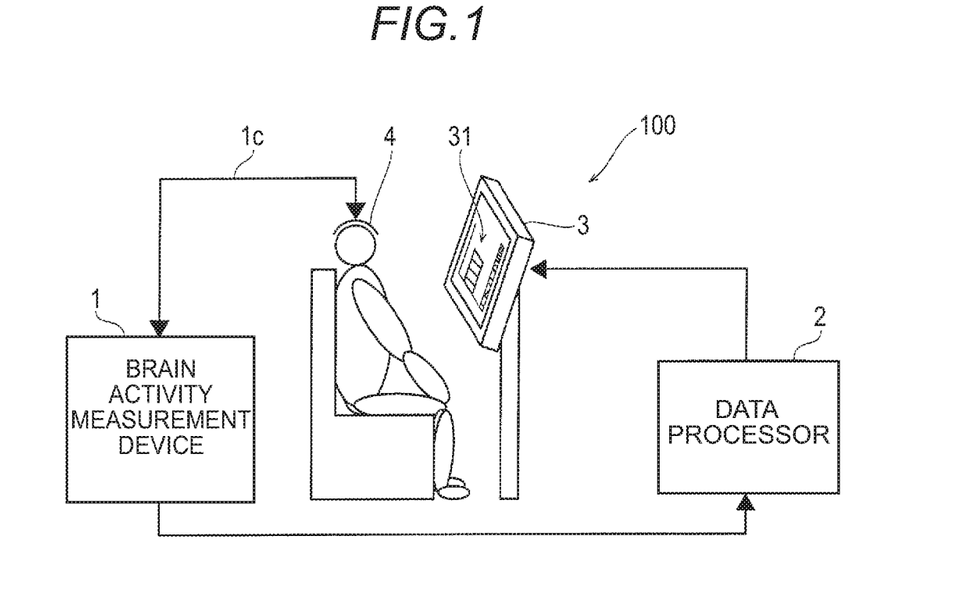
FIG. 1 is a schematic view illustrating the entire configuration of a brain activity feedback system according to one embodiment of the invention.

As illustrated in FIG. 1, the brain activity feedback system 100 according to this embodiment includes a brain activity measurement device 1, a data processor 2, and a display device 3. The data processor 2 is an example of a "data processing unit" of the invention. The display device 3 is an example of a "display unit" of the invention.

Figure 2:
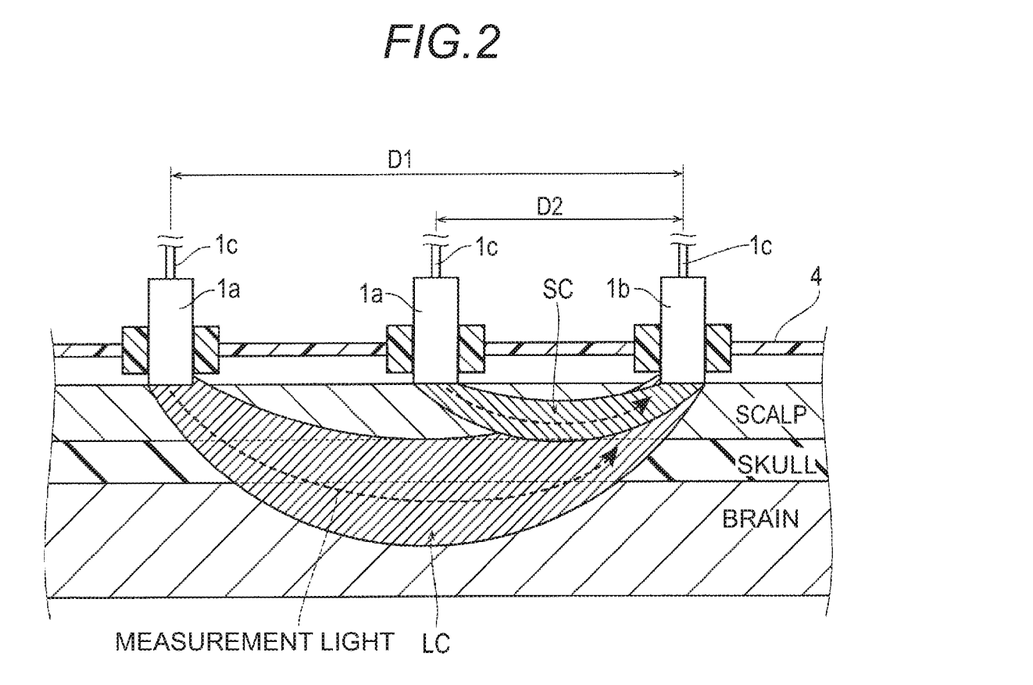
FIG. 2 is a schematic view for describing a first measurement channel and a second measurement channel.

First, the outline of the measurement of the brain activity according to the brain activity measurement device 1 will be described. The brain activity measurement device 1 is a device (a light measurement device) which optically measures brain activity of a subject by using a near-infrared spectroscopy (NIRS), and generates chronological measurement result data. Specifically, as illustrated in FIG. 2, the brain activity measurement device 1 applies measurement light in a wavelength range of near-infrared light from a light transmitting probe 1a disposed on the surface of the cephalic portion of the subject (a patient). Then, the brain activity measurement device 1 performs detection by allowing the measurement light reflected on the cephalic portion to be incident on a light receiving probe 1b disposed on the surface of the cephalic portion, and thus, the intensity of the measurement light (a light received amount) is acquired.

The brain activity measurement device 1 measures a change amount in oxygenated hemoglobin, deoxygenated hemoglobin, and the total hemoglobin, on the basis of the intensity of the measurement light (the light received amount) at a plurality of wavelengths (for example, three wavelengths of 780 nm, 805 nm, and 830 nm) and light absorption properties of hemoglobin. Accordingly, the brain activity measurement device 1 measures a brain blood flow change according to the brain activity as a change in a hemoglobin amount.

Figure 3:
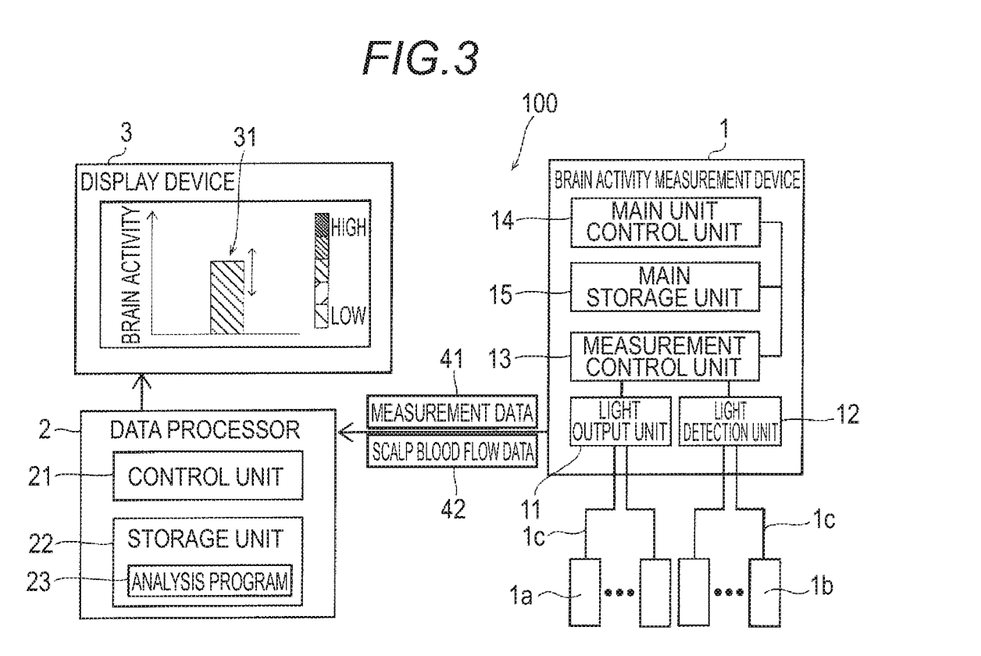
FIG. 3 is a block diagram illustrating configurations of a brain activity measurement device, a data processor, and a display device.

As illustrated in FIG. 3, the brain activity measurement device 1 includes a light output unit 11, a light detection unit 12, a measurement control unit 13, a main unit control unit 14, and a main storage unit 15. In addition, the brain activity measurement device 1 is connected to the light transmitting probe 1a and the light receiving probe 1b through an optical fiber 1c.

The light output unit 11 is configured to output the measurement light to the light transmitting probe 1a through the optical fiber 1c. The light output unit 11 includes a semiconductor laser or the like as a light source, and outputs the measurement light at the plurality of wavelengths in a wavelength range of near-infrared light. The light detection unit 12 is configured to include a photomultiplier tube or the like as a detector, acquire the measurement light incident on the light receiving probe 1b through the optical fiber 1c, and perform the detection.

The measurement control unit 13 performs operation control of the light output unit 11 and the light detection unit 12. The measurement control unit 13 controls a timing of turning on and off the light output unit 11, and acquires a signal of the light received amount from the light detection unit 12.

The main unit control unit 14 is a computer including a CPU, a memory, or the like, and is configured to execute various programs stored in the main storage unit 15, and thus, control a measurement operation of the brain activity measurement device 1.

In addition, the main unit control unit 14 is connected to the data processor 2 to communicate with each other, and transmits the obtained measurement data to the data processor 2. The measurement data is chronological data including measurement time (measurement timing) information and measurement value information for each measurement channel described below.

Figure 4:
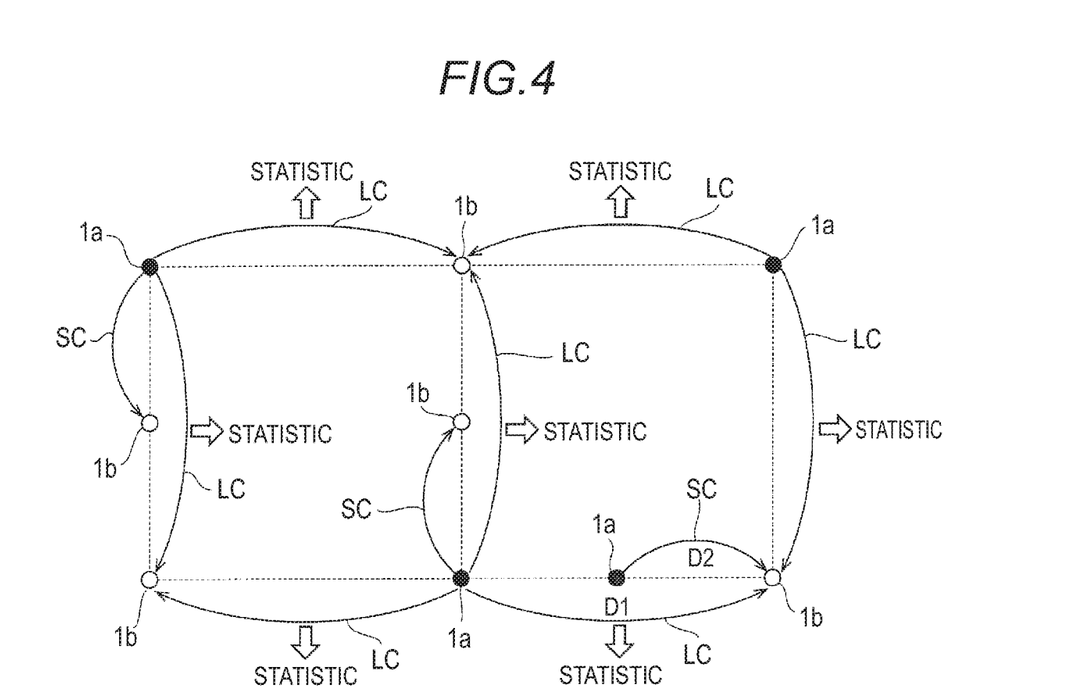
FIG. 4 is a schematic view illustrating the arrangement of the first measurement channel and the second measurement channel.

A plurality of light transmitting probes 1a and a plurality of light receiving probes 1b are provided, and a holder 4 (refer to FIG. 2) for fixing each of the probes is attached onto the surface of the cephalic portion in a predetermined position. A measurement channel (a measurement point) is formed between the adjacent light transmitting probe 1a and light receiving probe 1b. As illustrated in FIG. 4, the light transmitting probe 1a and the light receiving probe 1b are alternately arranged in each of a row direction and a column direction, in the holder 4.

In this embodiment, the brain activity measurement device 1 includes a first measurement channel LC and a second measurement channel SC having different probe distances, and performs measurement by each of two types of such measurement channels.

The first measurement channel LC is a channel which includes the light transmitting probe 1a and the light receiving probe 1b which are arranged in the cephalic portion of the subject with a predetermined first distance D1, and acquires measurement data 41 (refer to FIG. 3) of the brain activity. The second measurement channel SC is a channel which includes the light transmitting probe 1a and the light receiving probe 1b which are arranged in the cephalic portion of the subject with a second distance D2 less than the first distance D1, and acquires scalp blood flow data 42 (refer to FIG. 3).

As illustrated in FIG. 2, a probe distance affects a reaching depth into the cephalic portion of the measurement light, but on the structure of the human cephalic portion, even in a case where the probe distance is greater than a predetermined distance (approximately 3 cm), the reaching depth (a depth in a measurement position) is rarely changed. For this reason, in general, the first distance D1 for measuring the measurement data 41 of the brain activity (the brain blood flow change) is approximately 3 cm, and in this embodiment, such a value is adopted.

On the other hand, in a case where the probe distance is small, the measurement light passes through the scalp tissue (or the skull), and is detected out of the body without reaching the brain. For this reason, in the second measurement channel SC, it is possible to extract and measure a blood flow change (a scalp blood flow) in the scalp tissue. It is preferable that the second distance D2 for measuring the scalp blood flow has a size of less than or equal to ½ of the first distance D1. In order to extract only the scalp blood flow, it is preferable that the second distance D2 is small within a range allowed by the arrangement of the probes or the structure of the holder. In FIG. 2, an example is illustrated in which the second distance D2 is approximately ½ of the first distance D1.

A plurality of first measurement channels LC are provided according to the object of the measurement. It is preferable that the number of second measurement channels SC is less than or equal to the number of first measurement channels LC. In FIG. 4, an example is illustrated in which three second measurement channels SC are provided with respect to seven first measurement channels LC. The first measurement channel LC and the second measurement channel SC may include the common light transmitting probe 1a or the light receiving probe 1b as in the example of FIG. 4. A light transmitting timing and a light receiving timing of the light transmitting probe 1a and the light receiving probe 1b are individually controlled, and thus, it is possible to independently acquire the measurement data in each of the measurement channels.

In general, a task duration in which a task according to the object of the measurement of the brain activity is performed, and a rest duration in which the task is not performed are alternately repeated. A plurality of measurement channels are provided to be distributed in a predetermined region of the cephalic portion (the head surface) corresponding to an area of concern such that the brain activity in a brain region (the area of concern) relevant to the object of the measurement can be measured. For example, in the case of being used in rehabilitation for motor function recovery, a plurality of measurement channels are arranged in the predetermined region of the cephalic portion (the head surface) corresponding to the area of concern by setting a motor area or the like relevant to a motor function as the area of concern.

Next, device configurations of the data processor 2 and the display device 3 will be described.

As illustrated in FIG. 3, the data processor 2 includes a personal computer (PC) provided with a control unit 21 including a CPU, a memory, and the like, and a storage unit 22 such as a hard disk drive or a flash memory. The control unit 21 (CPU) executes an analysis program 23 stored in the storage unit 22, and the PC functions as the data processor 2 of the brain activity feedback system 100. The control unit 21 communicates with the brain activity measurement device 1, and thus, acquires the measurement data (the measurement data 41 of the first measurement channel LC and the scalp blood flow data 42 of the second measurement channel SC).

In this embodiment, the data processor 2 calculates a statistic (a t value) representing statistical significance of a change in the measurement data 41 reflecting the brain activity, on the basis of the measurement data 41 acquired from the brain activity measurement device 1. At this time, the data processor 2 is configured to correct a scalp blood flow component of the measurement data 41 on the basis of the scalp blood flow data 42, in real time, and calculate the statistic (the t value), with respect to the measurement data 41 acquired from the brain activity measurement device 1.

Specifically, the data processor 2 is configured to correct the scalp blood flow component in the measurement data 41 of the first measurement channel LC, on the basis of the scalp blood flow data 42 of the second measurement channel SC. The calculation of the statistic and the correction of the scalp blood flow component according to the data processor 2 will be described below.

The data processor 2 is connected to the display device 3, and is configured to output a video signal of a display screen including a brain activity index 31 corresponding to the calculated statistic to the display device 3.

The display device 3 displays the video signal of the brain activity index 31, which is output from the data processor 2. Accordingly, the display device 3 is configured to display the brain activity index 31 corresponding to the statistic in real time, and feeds back the brain activity index 31 to the subject.

The display device 3 is configured to change at least one of the shape and the color of a display representing the statistic, and display a change in the statistic as the brain activity index 31 in real time. Specifically, as illustrated in FIG. 3, the display device 3 displays the brain activity index 31 illustrated in the shape of a bar graph in which the statistic (the t value) is on a vertical axis. That is, in this embodiment, the statistic (the t value) displayed in a bar graph is adopted as the brain activity index 31. The display device 3 displays the height (the shape of the display) of the vertical axis of the brain activity index 31 in real time by changing the height, corresponding to the value of the statistic, which is calculated from the data processor 2 in real time.

Furthermore, in this embodiment, the data processor 2 is configured to acquire the measurement data 41 in a plurality of sites (the plurality of first measurement channels LC) in a predetermined area of concern, and display the brain activity index 31 corresponding to the maximum statistic (the t value) on the display device 3 from the statistic (the t value) of the measurement data 41 in the plurality of sites. For example, the measurement data 41 is obtained from the seven first measurement channels LC illustrated in FIG. 4, in the area of concern, and the maximum statistic (t value) of seven statistics (t values) calculated with respect to each measurement data 41 item is adopted as a value displaying a single bar graph of FIG. 3.

In addition, the display device 3 changes a display color of the brain activity index 31 according to the magnitude of the statistic (the t value). For example, the display device 3 sets a low value as a blue color and a high value as a red color, and continuously or gradually changes a color tone according to the size of the statistic. In FIG. 3, an example is illustrated in which the low value to the high value are divided into five steps (illustrated hatching instead of coloring), and a color corresponding to the statistic is displayed by being attached to the brain activity index 31.

[Calculation Method of Statistic and Calculation Method of Correction Amount of Scalp Blood Flow Component]

Next, a calculation method of the statistic and a calculation method of the correction amount of the scalp blood flow component will be described.

The statistic (the t value) is calculated with respect to the measurement data 41 in a predetermined time range by using a general linear model (GLM) and a sliding window. A time window 43 is set in a range (a time width) including at least one task duration. New measurement data 41 (a measurement value) is acquired, and the statistic (the t value) is calculated whenever the time window 43 is moved, and thus, the statistic (brain activity index 31) is fed back in real time.

In the general linear model, a measurement value $Y_s$ at time $t_s$ is represented by Expression (1) described below.

[Expression 1]

$$Y_s = \beta_0 + \beta_1 f^1(t_s) + \ldots + \beta_p f^p(t_s) + \varepsilon_s \qquad (1)$$

Here, each function f is a function representing a measurement model assumed in advance, each β is a coefficient (a regression coefficient) of the function f, and ε is an error.

In the case of expressing Expression (1) as a determinant including N measurement values of time $t_1$ to time $t_N$ included in the time window 43, Expression (2) described below is obtained.

[Expression 2]

$$\begin{bmatrix} Y_1 \\ Y_2 \\ \vdots \\ Y_N \end{bmatrix} = \begin{bmatrix} 1 & f^1(t_1) & \ldots & f^p(t_1) \\ 1 & f^1(t_2) & \ldots & f^p(t_2) \\ \vdots & \vdots & & \vdots \\ 1 & f^1(t_N) & \ldots & f^p(t_N) \end{bmatrix} \begin{bmatrix} \beta_0 \\ \beta_1 \\ \vdots \\ \beta_p \end{bmatrix} + \begin{bmatrix} \varepsilon_1 \\ \varepsilon_2 \\ \vdots \\ \varepsilon_N \end{bmatrix} \qquad (2)$$

すなわち, $Y = X \cdot \beta + \varepsilon$

That is

Y represents a chronological measurement value vector included in the time window 43, β represents a partial regression coefficient vector, and ε represents an error component. X is a matrix configured by a linear combination of the model function f, and is referred to as a design matrix.

Figure 5:
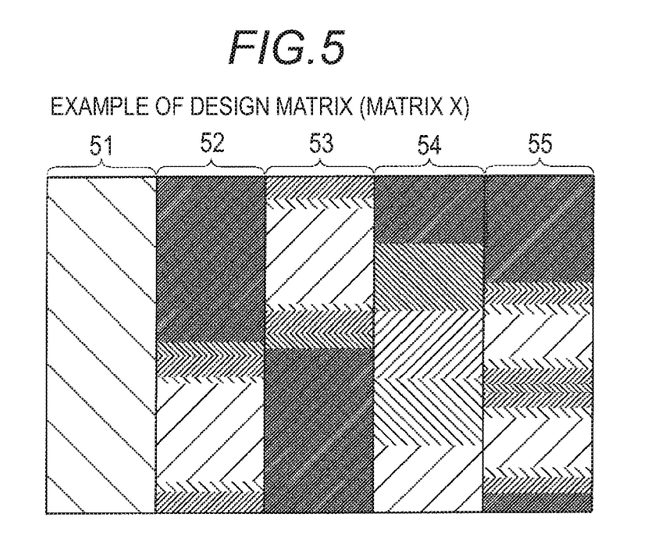
FIG. 5 is a diagram illustrating an example of a design matrix.

As illustrated in FIG. 5, the design matrix (the matrix X) is represented in a manner of expressing the magnitude of the value included in the matrix by gradation (in FIG. 5, expressed by hatching instead of gradation). The design matrix includes a plurality of model function vectors. Specifically, the design matrix includes a 0-dimensional function term 51, a task model function term 52, a rest model function term 53, and a 1-dimensional function term 54. In this embodiment, a scalp blood flow function term 55 is provided in the design matrix.

The 0-dimensional function term 51 is a constant term for offsetting the measurement value. The task model function term 52 and the rest model function term 53 are respectively a function which is assumed as a model representing measurement waveforms of a task period and a rest period. The task model function term 52 is obtained by convoluting a hemodynamic response function (HRF) in a boxcar function (a box type function having a value of 1 or 0) corresponding to the task period, and the rest model function term 53 is obtained by convoluting the hemodynamic response function in a boxcar function corresponding to the rest period. The task model function term 52 and the rest model function term 53 may respectively include a plurality of functions (a plurality of column vectors). The 1-dimensional function term 54 includes a 1-dimensional function for correcting a drift component of the measurement value.

The scalp blood flow function term 55 is a term (a column vector) for correcting the scalp blood flow component in the measurement data. By incorporating the scalp blood flow function term 55 in the design matrix, the scalp blood flow component is corrected, and the statistic (the t value) is calculated.

Figure 6:
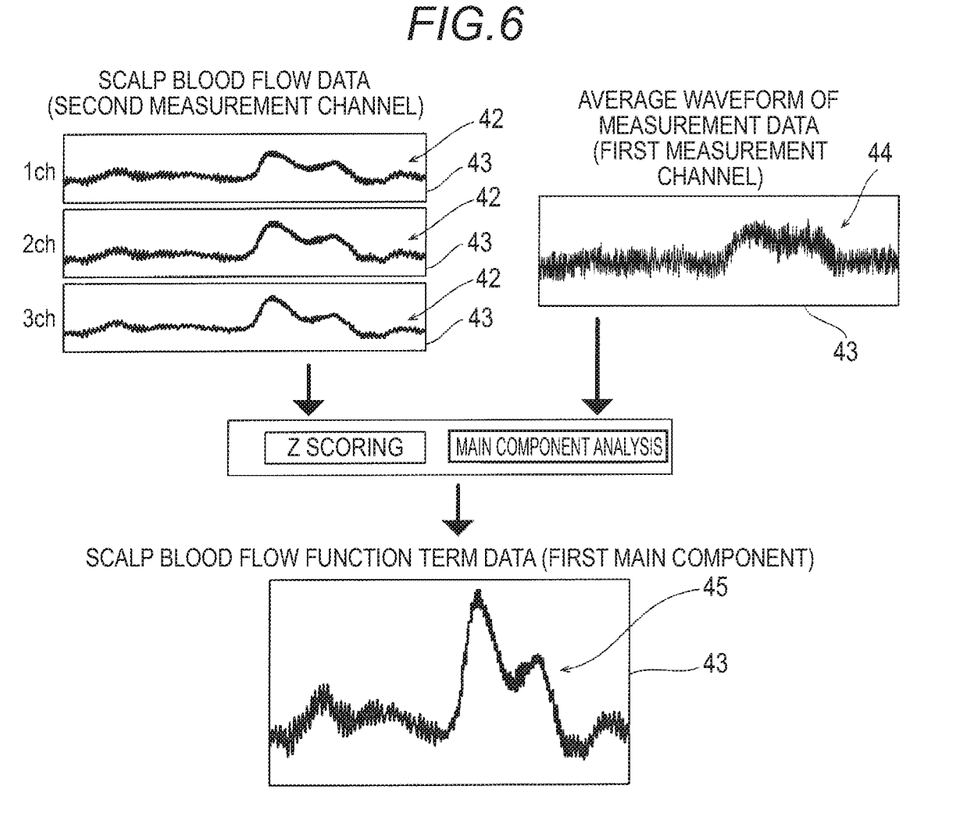
FIG. 6 is a conceptual diagram for describing data processing relevant to the correction of a scalp blood flow.

In this embodiment, the scalp blood flow function term 55 is calculated by using the scalp blood flow data 42 of a plurality of second measurement channels SC, and an average chronological change in the measurement data 41 of all of the first measurement channels LC. When the scalp blood flow function term 55 is calculated, as illustrated in FIG. 6, the data processor 2 (refer to FIG. 3) Z-scores (normalizes) each scalp blood flow data 42 item by using an average chronological change (an average waveform) 44 of the measurement data 41, and performs main component analysis with respect to each normalized scalp blood flow data 42 item.

A Z score is a value in which a set of chronological measurement data items is converted (normalized) such that the average is 0, and the standard deviation is 1. The average of the average chronological change 44 (the average waveform) of the measurement data 41 is set to A, the standard deviation is set to S, and a Z score z (t) is acquired by Expression (3) described below.

$$z(t)=(x-A)/S \quad (3)$$

According to Expression (3) described above, the size of the measurement data 41 and the scalp blood flow data 42 is normalized. Thus, in this embodiment, the data processor 2 normalizes the size of the component of the scalp blood flow function term 55 (a first main component 45 described below), on the basis of the scalp blood flow data 42 of the second measurement channel SC in the time window 43 (a predetermined time range), and the measurement data 41 (the average waveform of the measurement data 41) of the first measurement channel LC in the time window 43.

In addition, the data processor 2 calculates the first main component 45 which is obtained by performing the main component analysis with respect to the scalp blood flow data 42 of the plurality of second measurement channels SC, as the scalp blood flow function term 55. That is, the data processor 2 incorporates the obtained first main component 45 in the design matrix as the scalp blood flow function term 55. In other words, the data processor 2 corrects the scalp blood flow component of the measurement data 41 by using the obtained first main component 45 as the index of the scalp blood flow component included in the measurement data 41. The first main component 45 is an example of a "correction amount of a scalp blood flow component" of the invention.

In a case where the design matrix is determined, the data processor 2 calculates the statistic (the t value) by performing statistics analysis with respect to the general linear model illustrated in Expression (2) described above.

Specifically, the data processor 2 estimates the coefficient vector β on the basis of a measurement value Y (the measurement data 41 for predetermined time) included in the time window 43, and the design matrix X. A value, which is Z-scored as with the scalp blood flow data 42, is used as the measurement value Y. The coefficient vector β, for example, is estimated by fitting of obtaining the value of β which minimizes the error ε by a least-square method. In a case where the task model function term 52 and the rest model function term 53 are respectively one column (one column vector), the coefficient vector of Expression (2) described above includes β0 corresponding to the 0-dimensional function term 51, β1 corresponding to the task model function term 52 (one column), β2 corresponding to the rest model function term 53 (one column), β3 corresponding to the 1-dimensional function term 54, and β4 corresponding to the scalp blood flow function term 55.

The data processor 2 calculates the t value of a value obtained by subtracting the estimated β value (β2) corresponding to the first column of the rest period from the estimated β value (β1) corresponding to the first column of the task period, in the obtained coefficient vector β, and records the obtained t value as the statistic representing the statistical significance of the change in the measurement data reflecting the brain activity.

[Data Processing of Data Processor]

Next, data processing of the measurement data according to the data processor 2 will be described with reference to FIG. 3, FIG. 6, and FIG. 7. The following processing is performed by the control unit 21 (refer to FIG. 3) of the data processor 2.

Furthermore, the calculation of the statistic (the t value) is performed in real time starting from a time point where the number of data items for a time width of the time window 43 (the measurement data 41 and the scalp blood flow data 42 for predetermined time) is accumulated in the data processor 2, and then, by moving (sliding) the time window 43 whenever new data (the measurement data 41 and the scalp blood flow data 42) is acquired. In the following description, it is assumed that each data item for the time window 43 is in a state of being accumulated.

Figure 7:
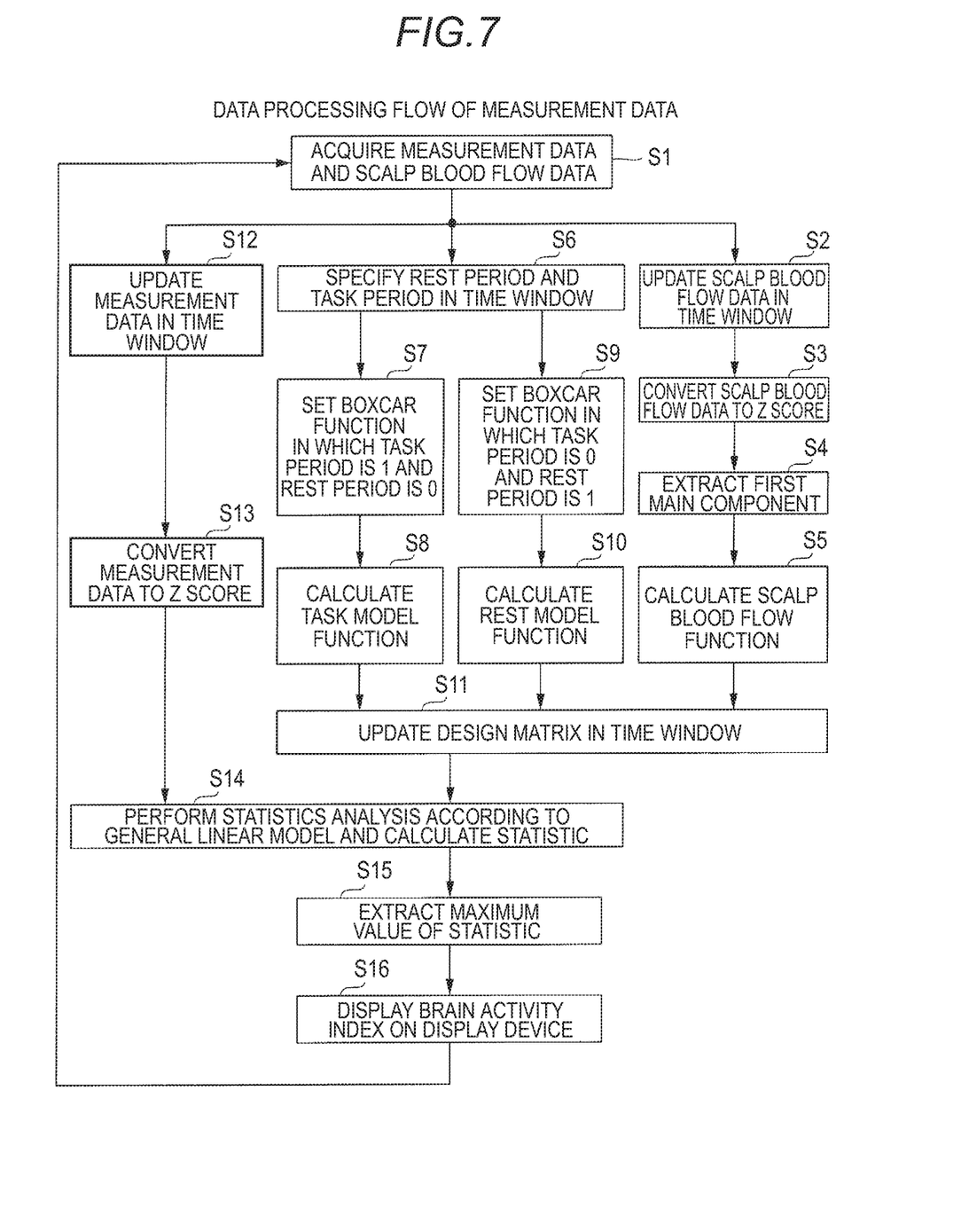
FIG. 7 is a flow diagram for describing data processing of measurement data according to the data processor.

First, in Step S1 of FIG. 7, the control unit 21 acquires new data from the brain activity measurement device 1, and records the data in the storage unit 22. The data to be acquired includes the measurement data 41 of the brain blood flow change according to the first measurement channel LC, and the scalp blood flow data 42 according to the second measurement channel SC. Hereinafter, the control unit 21 performs processing for determining the design matrix in the current time window 43, and processing of the measurement data 41 for the statistics analysis according to the general linear model, in parallel.

In the processing for determining the design matrix, in Step S2, the control unit 21 updates data arrangement of a plurality of (three in FIG. 6) scalp blood flow data 42 items in the time window 43 (slides each time window 43 to a time direction). In Step S3, the control unit 21 converts each of the scalp blood flow data 42 items in the time window 43 into a Z score. At this time, the control unit 21 converts (normalizes) the scalp blood flow data 42 into the Z score by using the average chronological change 44 (the average waveform) of the measurement data 41 of the first measurement channel LC obtained in Step S12 described below.

In Step S4, the control unit 21 performs the main component analysis with respect to the Z score of each of the normalized scalp blood flow data 42 items, and calculates the first main component 45 (refer to FIG. 6). As a result of Steps S2 to S4, in Step S5, the control unit 21 determines the data of the first main component 45 obtained from the scalp blood flow data 42 as the component of the scalp blood flow function term 55.

In addition, in Step S6, the control unit 21 specifies a time range corresponding to the task period in the time window 43, and a time range corresponding to the rest period, respectively.

In Step S7, the control unit 21 sets the boxcar function to have a value 1 in the task period in the current time window 43, and a value 0 in the rest period.

In Step S8, the control unit 21 convolutes the hemodynamic response function corresponding to the task period in the boxcar function set in Step S7, and calculates each component of the task model function term 52.

Similarly, in Step S9, the control unit 21 sets the boxcar function to have the value 1 in the rest period in the current time window 43, and the value 0 in the task period, and in Step S10, convolutes the hemodynamic response function corresponding to the rest period in the boxcar function set in Step S9, and calculates each component of the rest model function term 53.

Through Steps S5, S8, and S10 described above, in Step S11, the control unit 21 updates the data arrangement of the design matrix in the time window 43. At this time, the data of the 1-dimensional function term 54 is also updated. Accordingly, the design matrix (the matrix X) of Expression (2) described above in the current time window 43 is set.

On the other hand, in Step S12, the control unit 21 updates the data arrangement of the measurement data 41 of the first measurement channel LC included in the time window 43. Then, in Step S13, the control unit 21 converts the measurement data 41 of the first measurement channel LC in the obtained time window 43 into the Z score. Accordingly, the column vector of the measurement value Y of the measurement data 41 in Expression (2) described above is set.

Then, in Step S14, the control unit 21 performs the statistics analysis using the general linear model represented in Expression (2) described above. That is, the control unit 21 estimates the coefficient β from Expression (2) described above, and calculates the statistic (the t value) on the basis of the estimated β value in the task period and the estimated β value in the rest period. The control unit 21 calculates the statistic (the t value) for each of the first measurement channels LC, with respect to the measurement data 41 of all of the first measurement channels LC in the current time window 43. Furthermore, in the calculation of the statistic for each of the first measurement channels LC, the design matrix (the matrix X) including the scalp blood flow function term 55 is common.

In Step S15, the control unit 21 extracts the statistic (the t value) included in the area of concern set in advance from the statistic (the t value) for each of the first measurement channels LC, and acquires the maximum value in the extracted statistic (t value). Then, in Step S16, the control unit 21 outputs the video signal (the display screen) such that the obtained maximum value of the statistic (the t value) is displayed on the display device 3 as the brain activity index 31 (refer to FIG. 3) in the shape of a bar graph with a color.

The control unit 21 repeats the processing described above for each sampling period of the measurement data 41, and thus, updates and displays the brain activity index 31 on the display device 3 in real time, and feeds back the brain activity index 31 to the subject in real time.

[Effect of this Embodiment]

In this embodiment, the following effects can be obtained.

In this embodiment, as described above, the data processor 2 is configured to correct the scalp blood flow component of the measurement data 41 in real time, on the basis of the scalp blood flow data 42, and calculates the statistic (the t value), with respect to the measurement data 41 acquired from the brain activity measurement device 1. Accordingly, even in the case of feeding back (displaying) the brain activity index 31 according to the rehabilitation in real time, the scalp blood flow component of the measurement data 41 can be corrected in real time, and the statistic (the t value) can be calculated. As a result thereof, it is possible to calculate the statistic (the t value) in which the scalp blood flow component is corrected, in real time, and to display the brain activity index 31 corresponding to the statistic (the t value), and thus, it is possible to feed back the brain activity index 31 to the subject without decreasing accuracy even in real time.

In addition, in this embodiment, as described above, the first measurement channel LC acquiring the measurement data 41 by the light transmitting probe 1a and the light receiving probe 1b which are arranged with the first distance D1, and the second measurement channel SC acquiring the scalp blood flow data 42 by the light transmitting probe 1a and the light receiving probe 1b which are arranged with the second distance D2 less than the first distance D1, are provided in the brain activity measurement device 1. Then, the data processor 2 is configured to correct the scalp blood flow component in the measurement data 41 of the first measurement channel LC on the basis of the scalp blood flow data 42 of the second measurement channel SC. Accordingly, it is possible to obtain both of the measurement data 41 of the brain activity and the scalp blood flow data 42 by the common brain activity measurement device 1 without providing a dedicated device for measuring the scalp blood flow data 42. In addition, it is possible to acquire the scalp blood flow data 42 along with the measurement data 41 of the brain activity in parallel, and thus, it is possible to accurately correct the scalp blood flow component even in real time.

In addition, in this embodiment, as described above, the second distance D2 has a size of less than or equal to ½ of the first distance D1. Accordingly, it is possible to allow the measurement light to pass through only a shallow range from the scalp, and thus, it is possible to obtain the scalp blood flow data 42 which more accurately reflects the scalp blood flow. As a result thereof, it is possible to more accurately correct the scalp blood flow component.

In addition, in this embodiment, as described above, the data processor 2 is configured to calculate the correction amount of the scalp blood flow component in which the size is normalized (the first main component 45) on the basis of the scalp blood flow data 42 of the second measurement channel SC in the time window 43 in a predetermined time range, and the measurement data 41 of the first measurement channel LC in the time window 43 (the average chronological change 44 of the measurement data 41). Accordingly, it is possible to suitably correct the scalp blood flow component of the first measurement channel LC in different measurement sites from the local scalp blood flow data 42 from the second measurement channel SC, which is a relative change amount of the hemoglobin concentration.

In addition, in this embodiment, as described above, the data processor 2 is configured to calculate the first main component 45 obtained by performing the main component analysis with respect to the scalp blood flow data 42 of the plurality of second measurement channels SC, as the correction amount of the scalp blood flow component. Accordingly, it is possible to correct the scalp blood flow component without depending on the local scalp blood flow change by using the first main component 45 extracted from the scalp blood flow component data of the plurality of second measurement channels SC. In addition, it is possible to increase the data point used for calculating the correction amount, and thus, it is possible to more accurately correct the scalp blood flow component.

In addition, in this embodiment, as described above, the display device 3 is configured to display a change in the statistic (the t value) as the brain activity index 31, in real time, by changing at least one of the shape and the color of the display representing the statistic (the t value). Accordingly, it is possible to easily visually grasp a temporal change in the brain activity, and thus, it can be expected to improve the motivation of the rehabilitation with respect to the subject (the patient).

In addition, in this embodiment, as described above, the data processor 2 is configured to acquire measurement data 41 in the plurality of sites (the plurality of first measurement channels LC) in the area of concern, and display the brain activity index 31 corresponding to the maximum statistic (t value) from the statistic (the t value) of the measurement data in the plurality of sites on the display device 3. Accordingly, it is possible to feed back the brain activity index 31 in a simple and easy-to-grasp manner, to the subject (the patient), even in the case of calculating the statistic (the t value) for each of a plurality of first measurement channels LC. As a result thereof, it is possible to easily immediately grasp the brain activity, and thus, it can be expected to improve the motivation of the rehabilitation with respect to the subject (the patient).

[Modification Example]

Furthermore, the embodiment disclosed herein is merely an example in all points and is not restrictive. The scope of the invention is indicated by the scope of claims but not by the description of the embodiment, and includes all modifications (modification examples) within the equivalent meaning and the equivalent range to the scope of the claims.

For example, in the embodiment described above, an example has been described in which the brain activity feedback system 100 includes the brain activity measurement device 1, the data processor 2, and the display device 3, but the invention is not limited thereto. For example, the data processing unit may be provided in the brain activity measurement device. Specifically, a dedicated data processing unit may be provided in the brain activity measurement device 1, and the main unit control unit 14 of the brain activity measurement device 1 may be configured to execute the function of the control unit 21 of the data processor 2.

In addition, in the embodiment described above, an example has been described in which the measurement data 41 and the scalp blood flow data 42 are measured by the common brain activity measurement device 1, but the invention is not limited thereto. In the invention, the scalp blood flow data may be measured by a dedicated measurement device different from the brain activity measurement device.

In addition, in the embodiment described above, an example has been described in which the scalp blood flow component of the measurement data 41 is corrected by using the scalp blood flow data 42 of the plurality of second measurement channels SC, but the invention is not limited thereto. In the invention, the correction may be performed by using the scalp blood flow data of the single second measurement channel.

In addition, in the embodiment described above, an example has been described in which the first main component 45 obtained by performing the main component analysis with respect to the scalp blood flow data 42 of the plurality of second measurement channels SC is set to the correction amount of the measurement data 41 (each component of the scalp blood flow function term 55), but the invention is not limited thereto. In the invention, for example, the correction may be performed by using the scalp blood flow data of the second measurement channel.

Specifically, the first measurement channels LC and the second measurement channels SC of which the number is identical to the number of first measurement channels LC, are provided in the vicinity of each of the first measurement channels LC, and the measurement is performed such that the measurement data 41 of the first measurement channel LC corresponds to the scalp blood flow data 42 one on one. Then, the corresponding scalp blood flow data 42 is subtracted from the obtained measurement data 41, and thus, the scalp blood flow component may be corrected by using the measurement value of the scalp blood flow data 42. In addition, a value obtained by using a method such as an independent component analysis other than the main component analysis may be used as the correction amount of the measurement data 41 (each component of the scalp blood flow function term 55).

In addition, in the embodiment described above, an example has been described in which the scalp blood flow function term 55 is determined by using the scalp blood flow data 42 of the plurality of second measurement channels SC, and the average chronological change in the measurement data 41 of all of the first measurement channels LC, but the invention is not limited thereto. In the invention, the component of the scalp blood flow function term (the correction amount of the scalp blood flow) may be determined by using the measurement data in a part of the first measurement channel. For example, the scalp blood flow function term may be determined by only using a part of the first measurement channel measuring the brain region relevant to the object of the measurement (the area of concern).

In addition, in the embodiment described above, an example has been described in which the brain activity index 31 is displayed on the display device 3 in the shape of a bar graph and is fed back to the subject, but the invention is not limited thereto. In the invention, the brain activity index may be displayed in a shape other than the shape of a bar graph. For example, the brain activity index may be displayed in the shape of a line graph, a circle graph, or the like other than the bar graph. In addition, the brain activity index may be displayed by a numerical value, a mark, or the like other than the graph.

In addition, in the embodiment described above, an example has been described in which the brain activity index 31 having the value of the calculated statistic (t value) is displayed on the display device 3 in the shape of a bar graph, but the invention is not limited thereto. In the invention, the value of the calculated statistic (t value) may be converted into other indices for feedback, and then, may be used as the brain activity index.

In addition, in the embodiment described above, an example has been described in which the brain activity index 31 is displayed on the display device 3 in the shape of a bar graph with a color, but the invention is not limited thereto. In the invention, the brain activity index may not be displayed with a color, and a change in the brain activity index may be displayed by only a change in the color. For example, a display aspect may be used in which a schematic view illustrating an area of concern of the brain is displayed on the display device, and the color of the area of concern is changed according to the size of the statistic (the t value).

The invention claimed is:

1. A brain activity feedback system, comprising:
    a brain activity measurement device optically measuring brain activity of a subject;
    a data processing unit calculating a statistic representing statistical significance of a change in measurement data, which is acquired from the brain activity measurement device and reflects the brain activity, on the basis of the measurement data which is chronological data including measurement time information; and
    a display unit feeding back a brain activity index corresponding to the statistic to the subject by displaying the brain activity index, in real time,
    wherein the brain activity measurement device includes a first measurement channel acquiring the measurement data, and a second measurement channel acquiring scalp blood flow data of the subject,
    the data processing unit is configured to calculate the statistic by correcting a scalp blood flow component in the measurement data of the first measurement channel on the basis of a scalp blood flow function term for correcting the scalp blood flow component, in real time, and the data processing unit is configured to update the scalp blood flow function term for each sampling period of the measurement data on the basis of the measurement data and the scalp blood flow data.

2. The brain activity feedback system according to claim 1, wherein the first measurement channel is configured to acquire the measurement data by a light transmitting probe and a light receiving probe which are arranged in a cephalic portion of the subject with a predetermined first distance, and the second measurement channel is configured to acquire the scalp blood flow data by the light transmitting probe and the light receiving probe which are arranged in the cephalic portion of the subject with a second distance less than the first distance.

3. The brain activity feedback system according to claim 2, wherein the second distance has a size of less than or equal to ½ of the first distance.

4. The brain activity feedback system according to claim 2, wherein the data processing unit is configured to calculate a correction amount of the scalp blood flow component, which is the scalp blood flow function term, in which a size is normalized, on the basis of the scalp blood flow data of the second measurement channel in a predetermined time range, and the measurement data of the first measurement channel in the predetermined time range.

5. The brain activity feedback system according to claim 2, wherein the brain activity measurement device includes a plurality of second measurement channels, and the data processing unit is configured to calculate a first main component obtained by performing main component analysis with respect to the scalp blood flow data of the plurality of second measurement channels as a correction amount of the scalp blood flow component, which is the scalp blood flow function term.

6. The brain activity feedback system according to claim 1, wherein the display unit is configured to change at least one of a shape and a color of a display representing the statistic, and thus, to display a change in the statistic as the brain activity index, in real time.

7. The brain activity feedback system according to claim 1, wherein the data processing unit is configured to acquire the measurement data in a plurality of sites in a predetermined area of concern, and to display the brain activity index corresponding to the maximum statistic on the display unit from the statistic of the measurement data of the plurality of sites.

* * * * *